(12) United States Patent
Keller

(10) Patent No.: US 8,647,264 B1
(45) Date of Patent: Feb. 11, 2014

(54) MEDICAL DIAGNOSTIC SYSTEM FOR DETECTING INDICIA OF ACUTE OTITIS MEDIA

(76) Inventor: Jeffrey Lewis Keller, Chappaqua, NY (US)

( * ) Notice: Subject to any disclaimer, the term of this patent is extended or adjusted under 35 U.S.C. 154(b) by 46 days.

(21) Appl. No.: 12/932,844

(22) Filed: Mar. 8, 2011

Related U.S. Application Data

(60) Provisional application No. 61/340,228, filed on Mar. 15, 2010.

(51) Int. Cl.
*A61B 1/267* (2006.01)
(52) U.S. Cl.
USPC ........................................... 600/200
(58) Field of Classification Search
USPC ............ 600/184–200; 128/922; 382/128, 154
See application file for complete search history.

(56) References Cited

U.S. PATENT DOCUMENTS

| | | | | |
|---|---|---|---|---|
| 5,714,832 | A | * | 2/1998 | Shirrod et al. ................ 310/328 |
| 5,847,832 | A | * | 12/1998 | Liskow et al. ................ 356/613 |
| 2002/0038076 | A1 | * | 3/2002 | Sheehan et al. ............... 600/200 |
| 2008/0051637 | A1 | * | 2/2008 | Andreassen et al. .......... 600/200 |

* cited by examiner

*Primary Examiner* — Andrew Yang
*Assistant Examiner* — Diana S Jones

(57) ABSTRACT

A medical diagnostic system includes an otoscope, which is configured to generate at least a first image (e.g., digital photograph) of a tympanic membrane of a patient, and an apparatus for diagnosing acute otitis media within the patient. The apparatus includes a computer-readable storage medium having computer-readable program code embodied in the medium. The computer-readable program code includes a first computer-readable program code that evaluates the at least a first image of the tympanic membrane of the patient relative to a database containing at least one image of a tympanic membrane of at least one archived patient, to thereby detect indicia of acute otitis media in the patient.

12 Claims, 3 Drawing Sheets

MEDICAL DIAGNOSTIC SYSTEM FOR DETECTING INDICIA OF ACUTE OTITIS MEDIA

REFERENCE TO PRIORITY APPLICATION

This application claims priority to U.S. Provisional Application Ser. No. 61/340,228, filed Mar. 15, 2010, the disclosure of which is hereby incorporated herein by reference.

FIELD OF THE INVENTION

The present invention relates to medical diagnostic tools and, more particularly, to medical diagnostic tools for measuring physical properties of human tissues.

BACKGROUND OF THE INVENTION

Acute otitis media (AOM), which is one of the most common ailments in children, can be classified as an infectious inflammation in the middle ear that typically starts abruptly with significant pain, is of relatively short duration and can be clinically verified. Unfortunately, antibiotics, which are regularly recommended for the treatment of AOM, may not provide an optimum therapy for children suffering from AOM because spontaneous healing is frequent and regular antibiotic use may lead to widespread microbial resistance.

Myringotomy, which is a surgical procedure that involves the creation of a tiny incision in the eardrum to relieve pressure caused by an excessive build-up of fluid, is the most accurate technique for verifying the presence of AOM because it enables direct contact with any bacterial infection underneath the eardrum (i.e., within the middle ear). However, for most health care practitioners, including pediatricians, a diagnosis of AOM is typically based on a plurality of non-surgical symptoms. These symptoms may include earache, fever and reddening and/or bulging of the tympanic membrane within the ear canal. The use of a conventional otoscope to evaluate an outer surface of the tympanic membrane may not provide a conclusive determination of AOM because its symptoms frequently overlap with many other conditions of the ear that do not require antibiotic-based treatment. For example, an outward bulging of the tympanic membrane caused by the presence of fluid in the middle ear may result in reduced membrane mobility that suggests AOM. However, such bulging may actually be caused by otitis media with effusion (OME), which typically does not require any antibiotic-based treatment. Likewise, a reddening and thickening of the tympanic membrane with a loss of normal topology may suggest either AOM, OME or a common cold virus.

One system that purports to facilitate detection if AOM or OME in patients is disclosed in US Application Serial No. 2007/0112273 to Rogers, which is hereby incorporated herein by reference. This system includes an optical measuring unit and a control unit. The optical measuring unit is configured to irradiate a tympanic membrane of a patient with incident light having at least two different wavelengths and produce measurement data therefrom. The at least two different wavelengths are purportedly selected such that the response of the tympanic membrane from the first wavelength light is substantially independent of a predetermined condition to be detected, but the response from the second wavelength light is affected by the predetermined condition. Another system for measuring physical properties of tympanic membranes using reflected light is also disclosed in US Application Serial No. 2006/0282009 to Oberg et al., the disclosure of which is hereby incorporated herein by reference.

SUMMARY OF THE INVENTION

Medical diagnostic systems according to embodiments of the invention include an otoscope, which is configured to generate at least a first image (e.g., digital photograph) of a tympanic membrane of a patient, and an apparatus for diagnosing acute otitis media within the patient. This apparatus includes a computer-readable storage medium having computer-readable program code embodied in the medium. According to some of these embodiments of the invention, the computer-readable program code includes a first computer-readable program code that evaluates the at least a first image of the tympanic membrane of the patient relative to a database containing at least one image of a tympanic membrane of at least one archived patient, in order to thereby detect indicia of acute otitis media in the patient.

According to some of these embodiments of the invention, the at least one image of a tympanic membrane of the at least one archived patient is a second image of the tympanic membrane of the same patient taken under conditions when the patient was free of acute otitis media or other symptoms affecting the tympanic membrane. According to still further embodiments of the invention, the first computer-readable program code includes computer-readable program code that determines a maximum intensity of red light received from pixels in the first image. In addition, the first computer-readable program code includes computer-readable program code that determines: (i) an average intensity of red light received from pixels in the first image; and (ii) a first number of pixels in the first image having a red intensity greater than a first threshold intensity. This first threshold intensity is set at a level that is greater than an average intensity of red light received from pixels in the first image. In particular, the first threshold intensity may be determined based on an empirical analysis of a relatively large number of images of tympanic membranes associated with acute otitis media, which may have been confirmed using surgical procedures such as myringotomy. According to further aspects of these embodiments of the invention, the first computer-readable program code may include computer-readable program code that compares the first number against a number of pixels in the second image classified as having a red intensity in excess of a second threshold intensity. According to some embodiments of the invention, the second threshold intensity may be equivalent to the first threshold intensity.

According to still further embodiments of the invention, the otoscope is configured to generate a plurality of images of the tympanic membrane of the patient upon insertion into an ear canal of the patient. Each of these images may be focused on different regions of the tympanic membrane by virtue of capturing images of portions of the tympanic membrane at different planes of focus relative to a distal end of the otoscope. According to some of these embodiments of the invention, a primary one of the plurality of images will be focused on the tympanic membrane at a primary plane of focus using a conventional passive autofocus operation that seeks to maximize contrast over an entire image area, which may be a circular area that covers a substantial majority of the tympanic membrane. As will be understood by those skilled in the art of digital image capture, contrast measurements may be achieved by measuring contrast within a field of view, through adjustable lens elements extending proximate the distal end of the otoscope. In particular, because the intensity difference between adjacent pixels of an optical sensor array within the otoscope increase with more accurate image focus, intensity differences can be evaluated to determine an in-focus primary image. Thus, the optical system within the otoscope can be controlled using conventional digital image capture techniques until a maximum contrast is detected and the primary plane of focus is determined at a first distance from the otoscope.

According to still further embodiments of the invention, each of a plurality of secondary images of the tympanic membrane can be captured based on a measurement of contrast over a limited portion of the entire tympanic membrane that is observable by lens elements within the otoscope. For example, each of a plurality of concentric rings of pixels within the optical sensor array may be independently evaluated for maximum focus/contrast in order to achieve a respective in-focus ring-shaped image. Each of these ring-shaped images may be located at a different plane of focus relative to the primary plane of focus and, therefore, at a different distance from the distal end of the otoscope relative to the primary plane of focus.

By performing these image capture operations, second computer-readable program code may be provided within the computer readable storage medium to generate a first topographical map of the tympanic membrane from the primary and secondary images of the tympanic membrane. This first topographical map may provide information about the relative planarity, convexity and/or concavity of the tympanic membrane, with a higher degree of convexity suggesting a higher degree of outward membrane bulging caused by fluid pressure in the middle ear of the patient. For example, the relative convexity of a tympanic membrane may be determined by evaluating a change in distance between an outermost ring-shaped image of the tympanic membrane, which may be farther from the otoscope relative to the primary plane of focus, and an innermost ring-shaped (or spot) image of the tympanic membrane, which may be closer to the otoscope relative to the primary plane of focus.

The second computer-readable program code may also include computer-readable program code that compares the first topographical map to at least one topographical map of a tympanic membrane stored in the database, to thereby detect indicia of acute otitis media in the patient. In particular, the second computer-readable program code may include computer-readable program code that compares the first topographical map relative to at least one topographical map of an archived tympanic membrane of the same patient stored in the database. For example, in the event the first topographical map of the tympanic membrane of the patient demonstrates a higher degree of convexity relative to an archived topographical map of the same tympanic membrane of the same patient evaluated by equivalent means, then an indication that acute otitis media may be present.

According to still further embodiments of the invention, the otoscope may be configured to stimulate the tympanic membrane of the patient using conventional tympanometric techniques, which enable a compliance (i.e., mobility) of the tympanic membrane to be assessed. The otoscope is further configured to pass tympanometric data derived from the assessment of compliance to the apparatus. In addition, the computer-readable program code within the apparatus may include third computer-readable program code that evaluates the tympanometric data to assess a presence of acute otitis media in the patient. This evaluation may include generating a tympanogram and using conventional techniques to evaluate key characteristics of the tympanogram that affect a pathology diagnoses, such as peak pressure, compliance (maximum displacement) and width (gradient) of the tympanogram. Acute otitis media may be indicated by a depressed compliance peak amplitude and a negative pressure peak.

DESCRIPTION OF PREFERRED EMBODIMENTS

Figure 1A:
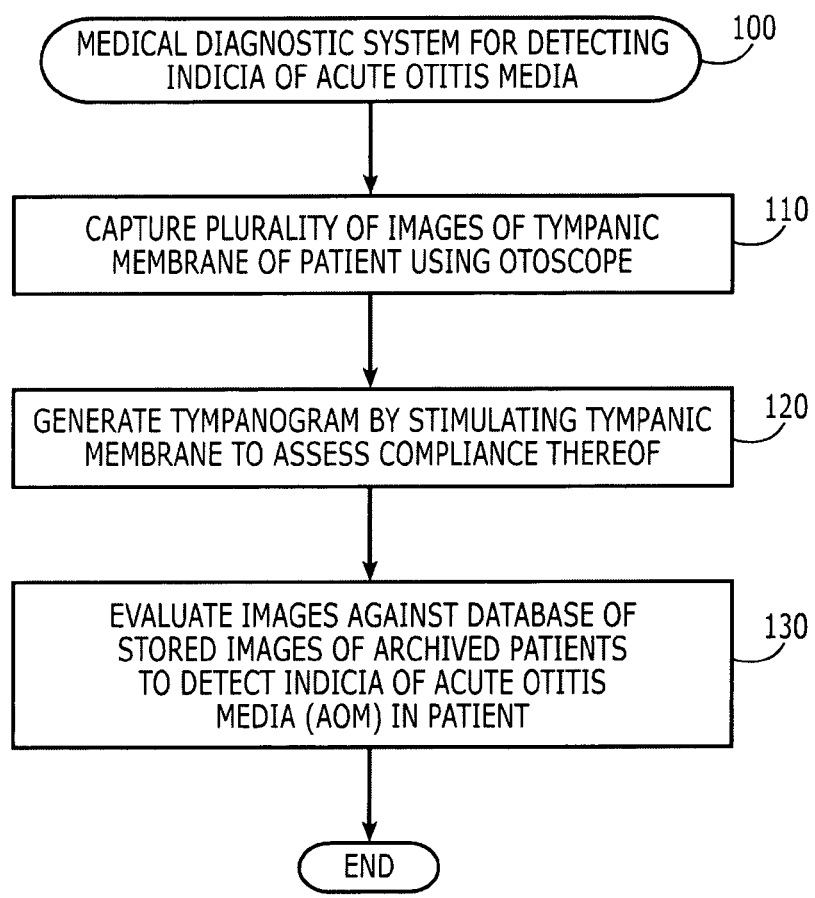
FIGS. 1A-1C are flow diagrams that illustrate operations performed by a medical diagnostic system according to embodiments of the invention. The medical diagnostic system includes an otoscope having digital image capture capability and an apparatus for diagnosing acute otitis media. This apparatus uses a computer-readable storage medium having a database of patient data stored therein in addition to computer-readable program code that evaluates the database of patient data against data provided by the otoscope contemporaneously with patient examination.

The present invention now will be described more fully with reference to the accompanying drawings, in which preferred embodiments of the invention are shown. This invention may, however, be embodied in many different forms and should not be construed as being limited to the embodiments set forth herein; rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprising", "including", having" and variants thereof, when used in this specification, specify the presence of stated features, steps, operations, elements, and/or components, but do not preclude the presence or addition of one or more other features, steps, operations, elements, components, and/or groups thereof. In contrast, the term "consisting of" when used in this specification, specifies the stated features, steps, operations, elements, and/or components, and precludes additional features, steps, operations, elements and/or components.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1A is a flow diagram that highlights operations 100 performed by a medical diagnostic system according to some embodiments of the invention. This system performs operations that enable an automated detection of indicia of acute otitis media (AOM) in a patent undergoing examination by a health care professional (e.g., pediatrician). As illustrated by Block 110, the system includes an otoscope having, among other things, digital image capture capability. During patient examination, this otoscope may operate to automatically capture a plurality of images of a tympanic membrane of the patient upon insertion of a distal end of an optical/pneumatic port of the otoscope into an ear canal of the patient. Conventional operations may then be performed by the otoscope and apparatus to generate a tympanogram of the tympanic membrane within the ear canal, Block 120. These operations include pneumatically stimulating the tympanic membrane to assess, among other things, compliance/mobility of the membrane. Referring now to Block 130, the tympanogram and the plurality of images are evaluated against a database of stored images of archived patients to facilitate detection of indicia of acute otitis media (AOM) in the patient.

Figure 1B:
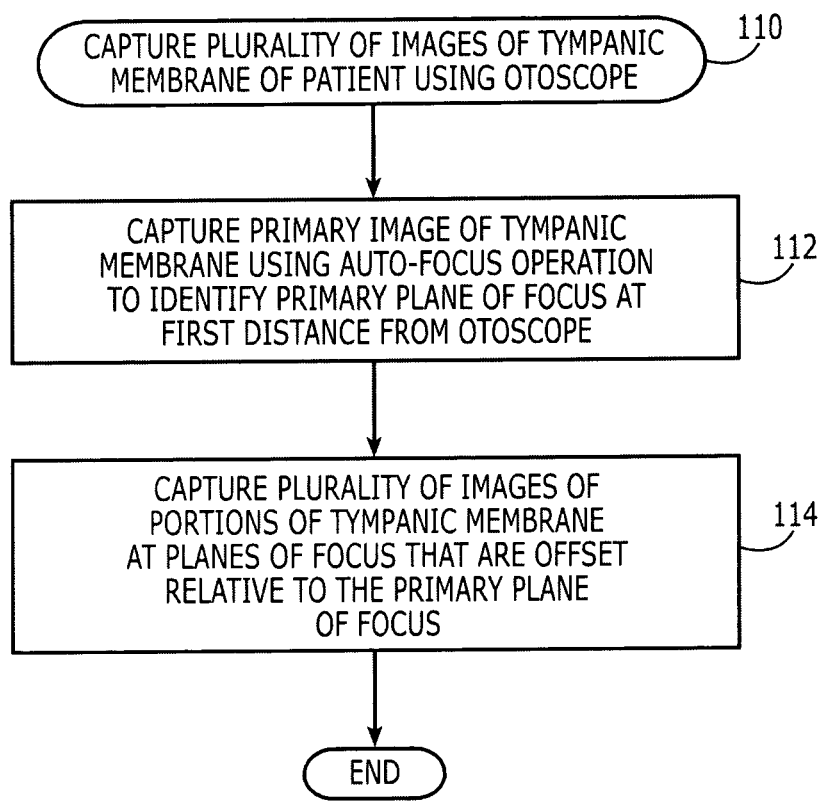

Referring now to FIG. 1B, the operations performed by Block 110 in FIG. 1A may include capturing a primary image of the tympanic membrane of the patient using an auto-focus operation. These operations are performed to identify a primary plane of focus on the membrane located at a first distance from the otoscope, Block 112. The operations 110 may also include capturing a plurality of images of portions of the tympanic membrane at planes of focus that are offset relative to the primary plane of focus, Block 114. For example, a relatively small "spot" image located at a center of the tympanic membrane and a plurality of concentric ring-shaped images of the membrane taken at increasing radii relative to the spot image may be captured at respective planes of focus. These operations, which are more fully illustrated by Blocks 114a-114c of FIG. 1C, include capturing an outermost ring-shaped image at one plane of focus, Block 114a, capturing a spot-shaped image at another plane of focus, Block 114c, and capturing a plurality of interior concentric ring-shaped images at respective planes of focus, Block 114b. Because each of these planes of focus for a typical non-planar tympanic membrane correlate to different distances between the spot or ring-shaped planes and the otoscope, a calculation of the degree of convexity of the tympanic membrane can be readily made using conventional geometric operations. When immediately compared against a database of stored images of tympanic membranes and corresponding convexity values, including archived membrane images taken from the same patient under conditions demonstrating an absence of any disease, real-time evidence of disease-based bulging of the tympanic membrane can be identified. This evidence can then be used in conjunction with data derived from the tympanogram to assess the presence of AOM.

Figure 1C:
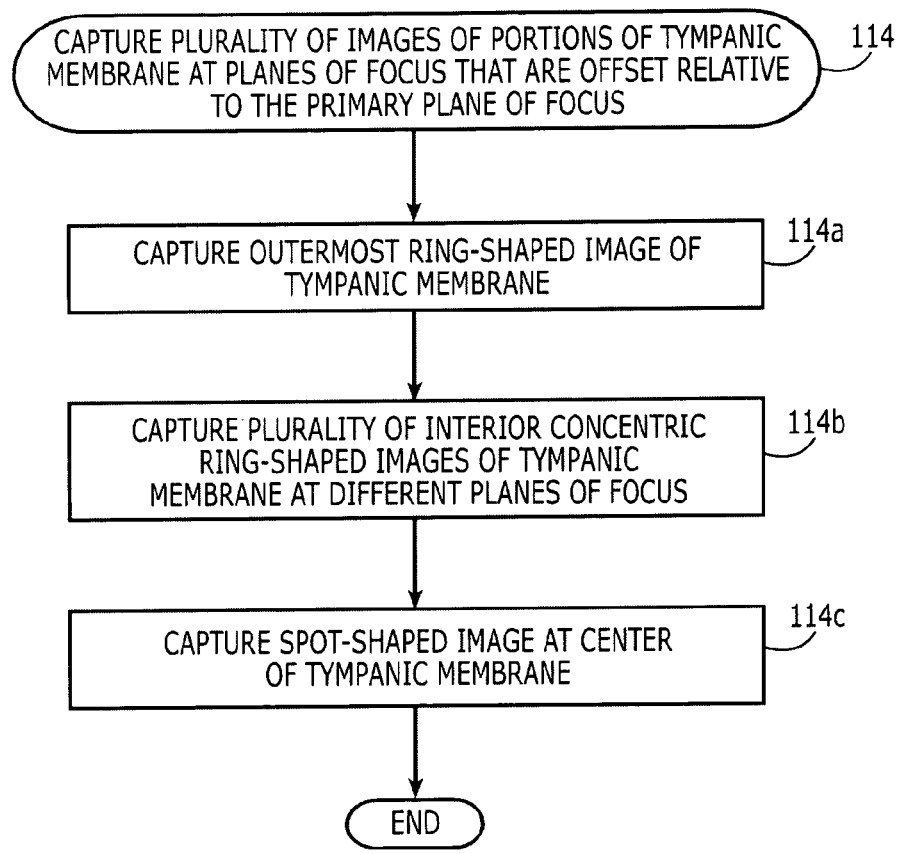

In addition to the operations highlighted by FIGS. 1A-1C, color data extracted from the primary image may be compared against color data associated with images stored in the database, to supplement the real-time assessment of the possible presence of AOM. For example, the apparatus may include first computer-readable program code that determines: (i) a maximum intensity of red light received from pixels in the primary image, (ii) an average intensity of red light received from the pixels in the primary image; and (iii) a first number of pixels in the primary image having a red intensity greater than a first threshold intensity. This first threshold intensity is set at a level that is greater than an average intensity of red light received from pixels in the primary image. In particular, the first threshold intensity may be determined based on an empirical analysis of a relatively large number of images of tympanic membranes associated with acute otitis media, which may have been confirmed using surgical procedures such as myringotomy.

According to further aspects of these embodiments of the invention, the first computer-readable program code may include computer-readable program code that compares the first number against a number of pixels in a corresponding archived image of the same tympanic membrane, which are determined as having a red intensity in excess of a second threshold intensity. This second threshold intensity is typically equivalent to the first threshold intensity. In this manner, any increase in a degree of redness in the primary image relative to a corresponding archived image, can be detected and used to supplement the automated determination of AOM.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A medical diagnostic system, comprising:
   an otoscope configured to generate at least a first image of a tympanic membrane of a patient; and
   an apparatus for diagnosing acute otitis media within the patient, said apparatus comprising a computer-readable storage medium having computer-readable program code embodied in said medium, said computer-readable program code comprising:
     first computer-readable program code for evaluating the at least a first image of the tympanic membrane of the patient relative to a second image of the patient taken under conditions when the patient was free of acute otitis media, to thereby detect indicia of acute otitis media in the patient;
   wherein said otoscope is further configured to capture a plurality of ring-shaped images of portions of the tympanic membrane of the patient that are focused at respective points on the tympanic membrane, which are located at different planes of focus relative to said otoscope; and
   wherein said computer-readable program code further comprises second computer-readable program code for generating a first topographical map of the tympanic membrane of the patient from the plurality of ring-shaped images by evaluating a change in distance between a first one of the plurality of ring-shaped images of the tympanic membrane at a first plane of focus and another image of at least a portion of the tympanic membrane at a second plane of focus, relative to said otoscope.

2. The medical diagnostic system of claim 1, wherein said first computer-readable program code comprises computer-readable program code for determining a maximum intensity of red light received from pixels in the first image.

3. The medical diagnostic system of claim 2, wherein said first computer-readable program code comprises computer-readable program code for determining a first number of pixels in the first image having a red intensity greater than a first threshold intensity that is greater than an average intensity of red light received from pixels in the first image.

4. The medical diagnostic system of claim 3, wherein said first computer-readable program code comprises computer-readable program code for comparing the first number against a number of pixels in the second image classified as having a red intensity in excess of a second threshold intensity.

5. The medical diagnostic system of claim 1, wherein said second computer-readable program code comprises computer-readable program code for comparing the first topographical map relative to at least one topographical map of tympanic membrane of the patient stored in a database, to thereby detect indicia of acute otitis media in the patient.

6. The medical diagnostic system of claim 1, wherein said otoscope is further configured to stimulate the tympanic membrane of the patient under conditions that enable a mobility of the tympanic membrane to be assessed.

7. The medical diagnostic system of claim 6, wherein said otoscope is further configured to pass tympanometric data to said apparatus; and wherein said computer-readable program code comprises third computer-readable program code for evaluating the tympanometric data to assess a presence of acute otitis media in the patient.

8. The medical diagnostic system of claim 1, wherein the plurality of ring-shaped images of portions of the tympanic membrane of the patient are concentric.

9. The medical diagnostic system of claim 8, wherein said evaluating comprises evaluating a change in distance between an outermost ring-shaped image of the tympanic membrane and an innermost spot image of the tympanic membrane, relative to said otoscope.

10. The medical diagnostic system of claim 1, wherein said evaluating comprises evaluating a change in distance between an outermost ring-shaped image of the tympanic membrane and an innermost ring-shaped or spot image of the tympanic membrane, relative to said otoscope.

11. A medical diagnostic system, comprising:
  an apparatus for diagnosing acute otitis media within a patient, said apparatus comprising a computer-readable storage medium having computer-readable program code embodied in said medium, said computer-readable program code comprising:
    computer-readable program code for comparing a first topographical map of a tympanic membrane of a patient against a second topographical map of a tympanic membrane of the patient taken under conditions when the patient was free of acute otitis media, to thereby detect differences between the first and second topographical maps, said first topographical map generated by evaluating a change in distance between a plurality of concentrically-arranged ring-shaped or spot images of portions of the tympanic membrane that are located at different planes of focus relative to a reference plane.

12. A medical diagnostic system, comprising:
an otoscope; and
an apparatus for diagnosing acute otitis media within a patient, said apparatus comprising a computer-readable storage medium having computer-readable program code embodied in said medium, said computer-readable program code comprising:
  first computer-readable program code for evaluating at least a first image of a tympanic membrane of the patient relative to a second image of the patient taken under conditions when the patient was free of acute otitis media, to thereby detect indicia of acute otitis media in the patient;
wherein said otoscope is configured to capture a plurality of concentrically-arranged ring-shaped and spot images of the tympanic membrane of the patient at respective different planes of focus; and
wherein said computer-readable program code further comprises second computer-readable program code for determining a degree of convexity of the tympanic membrane of the patient from the plurality of ring-shaped and spot images by evaluating a change in distance between the respective planes of focus of at least two of the plurality of concentrically-arranged ring-shaped and spot images of the tympanic membrane.

* * * * *